United States Patent
Hashimoto et al.

(10) Patent No.: US 6,461,300 B2
(45) Date of Patent: Oct. 8, 2002

(54) ULTRASONIC IMAGING APPARATUS AND METHOD OF INDICATING THE NEXT SCANNING START TIME

(75) Inventors: Hiroshi Hashimoto, Tokyo (JP); Kow Tanaka, Tokyo (JP); Teruo Anzai, Tokyo (JP); Ken Kanno, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/928,179

(22) Filed: Aug. 10, 2001

(65) Prior Publication Data

US 2002/0042573 A1 Apr. 11, 2002

(30) Foreign Application Priority Data

Oct. 10, 2000 (JP) ......................................... 2000-308668

(51) Int. Cl.[7] ................................................. A61B 8/00
(52) U.S. Cl. ....................................... 600/437; 600/458
(58) Field of Search ................................. 600/447, 454, 600/456, 440, 453, 443, 437–472

(56) References Cited

U.S. PATENT DOCUMENTS

| | | | | |
|---|---|---|---|---|
| 5,052,395 A | * | 10/1991 | Burton et al. | 600/454 |
| 5,158,088 A | * | 10/1992 | Nelson et al. | 600/461 |
| 5,469,849 A | * | 11/1995 | Sasaki et al. | 600/443 |
| 5,505,204 A | * | 4/1996 | Picot et al. | 600/456 |
| 5,560,364 A | * | 10/1996 | Porter | 600/458 |
| 5,848,968 A | * | 12/1998 | Takeuchi | 600/458 |
| 5,935,069 A | * | 8/1999 | Chandler et al. | 600/439 |

* cited by examiner

Primary Examiner—Francis J. Jaworski
Assistant Examiner—William C. Jung
(74) Attorney, Agent, or Firm—Moonray Kojima

(57) ABSTRACT

An ultrasonic imaging apparatus indicates the preceding time length which lasts until the next scanning start time on a bar graph or the like, thereby relieving the operator's duty in carrying out intermittent scanning.

14 Claims, 12 Drawing Sheets

ULTRASONIC IMAGING APPARATUS AND METHOD OF INDICATING THE NEXT SCANNING START TIME

BACKGROUND OF THE INVENTION

The present invention relates to an ultrasonic imaging apparatus, and particularly to an ultrasonic imaging apparatus which implements repeatedly and intermittently the ultrasonic wave transmit/receive operation of scanning the inside of a subject with an ultrasonic wave and receiving an echo of the ultrasonic wave, with a predetermined resting period being interposed between operations.

Ultrasonic imaging utilizes the echo of an ultrasonic wave which is radiated to the inside of a subject to produce a tomographic image of the subject, and displays a resulting B-mode image. It also utilizes the Doppler shift of the ultrasonic echo to produce an image of the dynamic state of a blood flow or the like, and displays a resulting color Doppler image.

If it is needed to raise the magnitude of echo, the region of interest is filled with contrast agent by utilization of the blood flow. The contrast agent is a mass of fine bubbles having a diameter of several $\mu$m.

The contrast agent dissolves by being hit by an ultrasonic wave and thereafter does not produce an echo, and therefore next scanning is carried out by being timed so that the imaging portion is filled with contrast agent again.

On this account, ultrasonic imaging based on the use of contrast agent implements the intermittent scanning having a resting period of several seconds to several tens of seconds in each operation cycle. A tomographic image produced by each scanning is displayed as a frozen image, and it is revised at each scan-imaging.

In the intermittent scanning operation, the operator of ultrasonic imaging apparatus must keep to put the ultrasonic probe on the imaging portion of the subject preparatory to the next scanning, and it is a hard work for the operator to stay tight even during the resting period of intermittent scanning.

SUMMARY OF THE INVENTION

Accordingly, it is an object of the present invention to accomplish an ultrasonic imaging apparatus which relieves the operator's duty in the intermittent scanning operation.

The present invention for solving the above-mentioned problems resides in an ultrasonic imaging apparatus comprising ultrasonic wave transmission/reception means which implements repeatedly and intermittently ultrasonic wave transmission/reception operations of scanning the inside of a subject with an ultrasonic wave and receiving an echo of the ultrasonic wave, with a predetermined resting period being interposed between operations, imaging means which produces an image based on the received echo, display means which displays the image, and indication means which indicates the length of preceding time which lasts up to the next scanning start time.

According to this invention, the preceding time length until the next scanning start time is indicated, and the operator can anticipate the start time of ultrasonic wave transmission/reception accurately and can relax and wait until then.

By displaying the preceding time length on a graph, the operator can recognize the preceding time length in analog fashion.

By displaying the preceding time length in terms of hues, the operator can recognize the preceding time length in steps.

By displaying the preceding time length numerically, the operator can recognize the preceding time length in digital fashion.

By displaying the preceding time length acoustically, both the operator and the person under test can recognize the preceding time length.

The present invention seen from another viewpoint for solving the above-mentioned problem resides in an ultrasonic imaging method which is characterized by implementing repeatedly and intermittently ultrasonic wave transmission/reception operations of scanning the inside of a subject with an ultrasonic wave and receiving an echo of the ultrasonic wave, with a predetermined resting period being interposed between operations, producing an image based on the received echo and displaying the image, and indicating the length of preceding time which lasts up to the next scanning start time. The invention of this viewpoint can achieve the same effectiveness as described above.

Therefore, the present invention can accomplish the ultrasonic imaging apparatus which relieves the operator's duty in carrying out the intermittent scanning.

Further objects and advantages of the present invention will be apparent from the following description of the preferred embodiments of the invention as illustrated in the accompanying drawings.

DETAILED DESCRIPTION OF THE INVENTION

Figure 1:
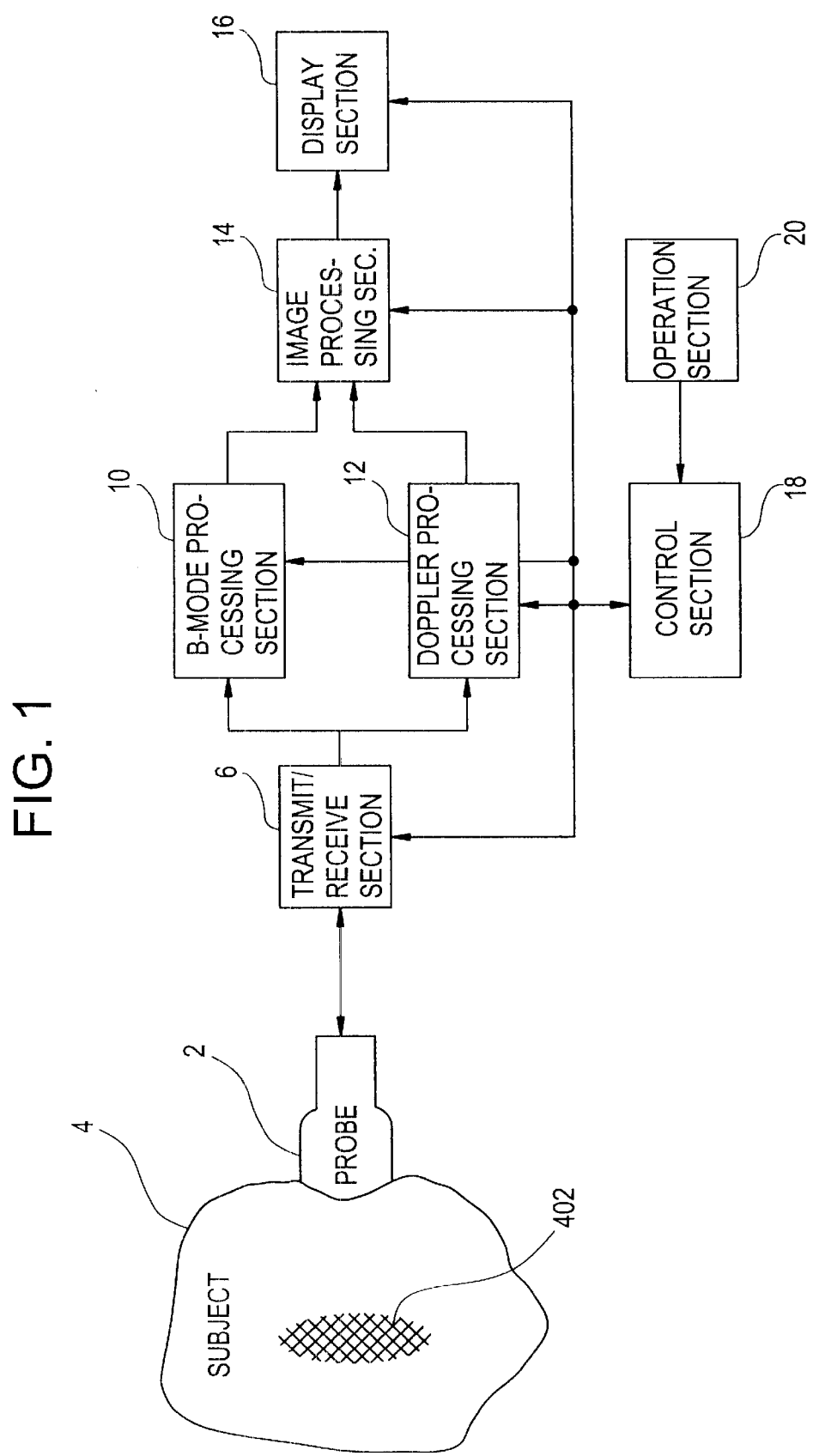
FIG. 1 is a block diagram of the apparatus which is an example of embodiment of this invention.

An embodiment of this invention will be explained in detail with reference to the drawings. FIG. 1 shows by block diagram an ultrasonic imaging apparatus, which is an example of embodiment of this invention. The arrangement of this apparatus shows an example of embodiment the inventive apparatus.

As shown in FIG. 1, this apparatus includes an ultrasonic probe 2. The ultrasonic probe 2 has an array of a number of ultrasonic transducers (not shown). Each ultrasonic transducer is formed of a piezoelectric material, e.g., PZT (titanium (Ti) acid zirconium (Zr) acid) ceramics. The ultrasonic probe 2 is used by the operator to come in contact with a subject 4. The subject 4 has its region of interest fed in advance with contrast agent 402 by utilization of the blood flow.

The ultrasonic probe 2 is connected to a transmit/receive section 6. The transmit/receive section 6 supplies a drive signal to the ultrasonic probe 2, which then transmits an ultrasonic wave. The transmit/receive section 6 gets an echo signal which is received by the ultrasonic probe 2.

Figure 2:
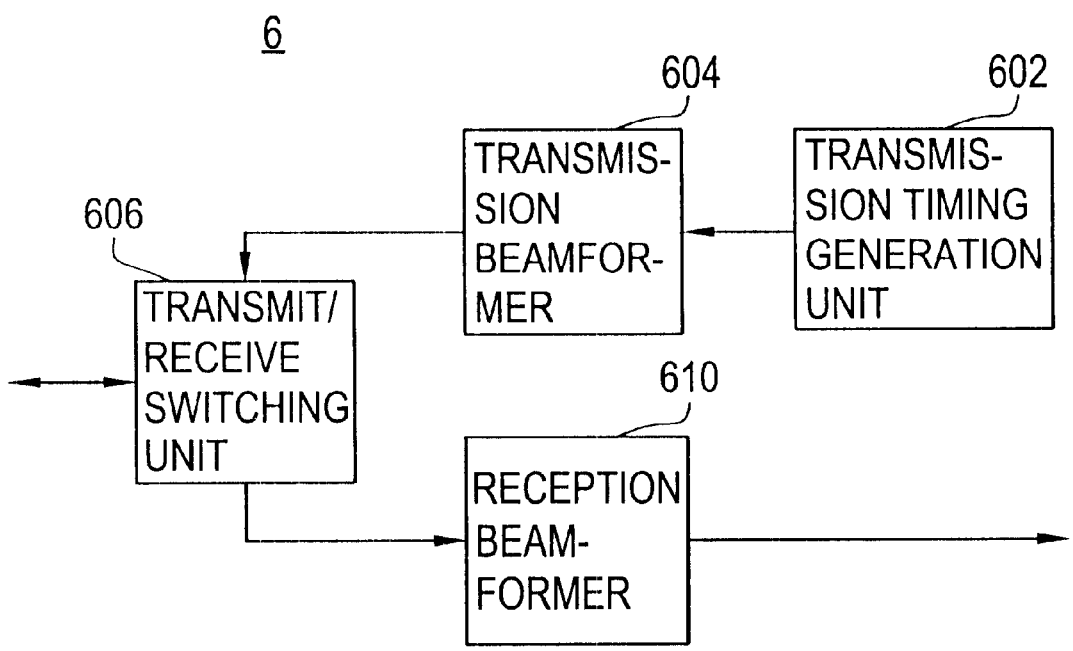
FIG. 2 is a block diagram of the transmit/receive section of the apparatus shown in FIG. 1.

FIG. 2 shows by block diagram the transmit/receive section 6. As shown in the figure, the transmit/receive section 6 includes a transmission timing generation unit 602. The transmission timing generation unit 602 generates a transmission timing signal periodically and puts the signal into a transmission beamformer 604. The transmission timing signal has its period controlled by a control section 18 which will be explained later.

The transmission beamformer 604, which implements the beamforming for transmission, produces a beamforming signal for making an ultrasonic beam of a prescribed azimuth based on the transmission timing signal. The beamforming signal consists of a number of drive signals having time differences which correspond to the azimuths. Beamforming is controlled by the control section 18 which will be explained later. The transmission beamformer 604 puts the transmission beamforming signal into a transmit/receive switching unit 606.

The transmit/receive switching unit 606 puts the beamforming signal into the ultrasonic transducer array. In the ultrasonic transducer array, the ultrasonic transducers which constitute transmission apertures generate ultrasonic waves having phase differences which correspond to the time differences of the drive signals. Based on the wave front composition of these ultrasonic waves, an ultrasonic beam along the line of a certain azimuth is made.

The transmit/receive switching unit 606 is connected to a reception beamformer 610. The transmit/receive switching unit 606 puts the echo signals, which have been received by reception apertures of the ultrasonic transducer array, into the reception beamformer 610. The reception beamformer 610, which implements the beamforming for reception in correspondence to the transmission sonic beam, makes time differences among received echoes to adjust their phases and subsequently sums the echoes to form an echo reception signal along the sonic beam of a certain azimuth. Beamforming of reception is controlled by the control section 18 which will be explained later.

Figure 3:
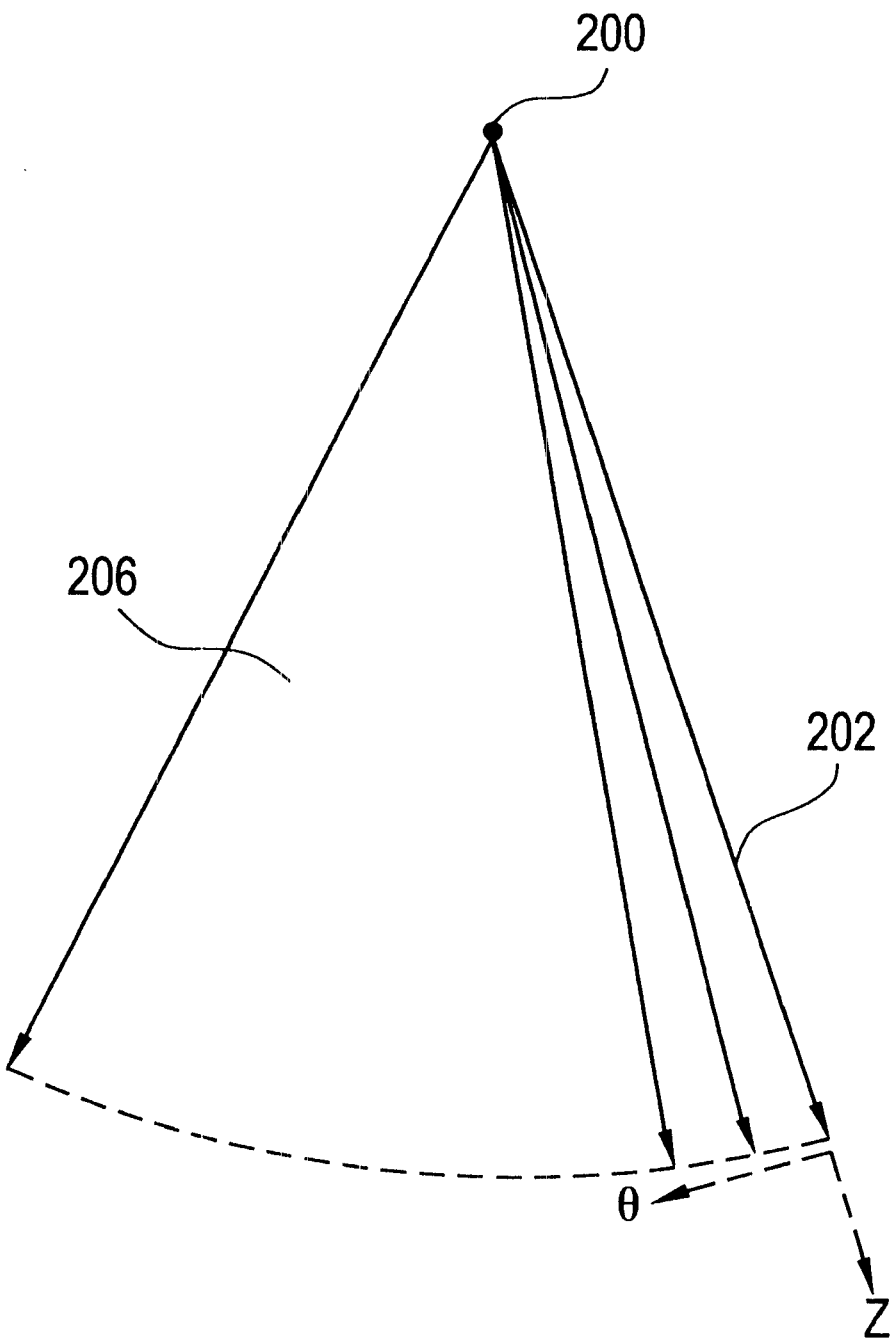
FIG. 3 is a schematic diagram of sonic beam scanning by the apparatus shown in FIG. 1.

Transmission of ultrasonic beam takes place repetitively at a certain time interval in response to the transmission timing signal generated by the transmission timing generation unit 602. In synchronism with the beam transmission, the transmission beamformer 604 and reception beamformer 610 alter the azimuth of sonic beam at a certain step. In consequence, the sonic beam scans the inside of the subject 4 in succession. The transmit/receive section 6 having this arrangement performs the scanning as shown in FIG. 3 for example. Specifically, it scans a two-dimensional sectoral region 206 along the direction of θ with a sonic beam 202 extending in the z direction from a radiation point 200, thereby performing so-called sector scanning.

Figure 4:
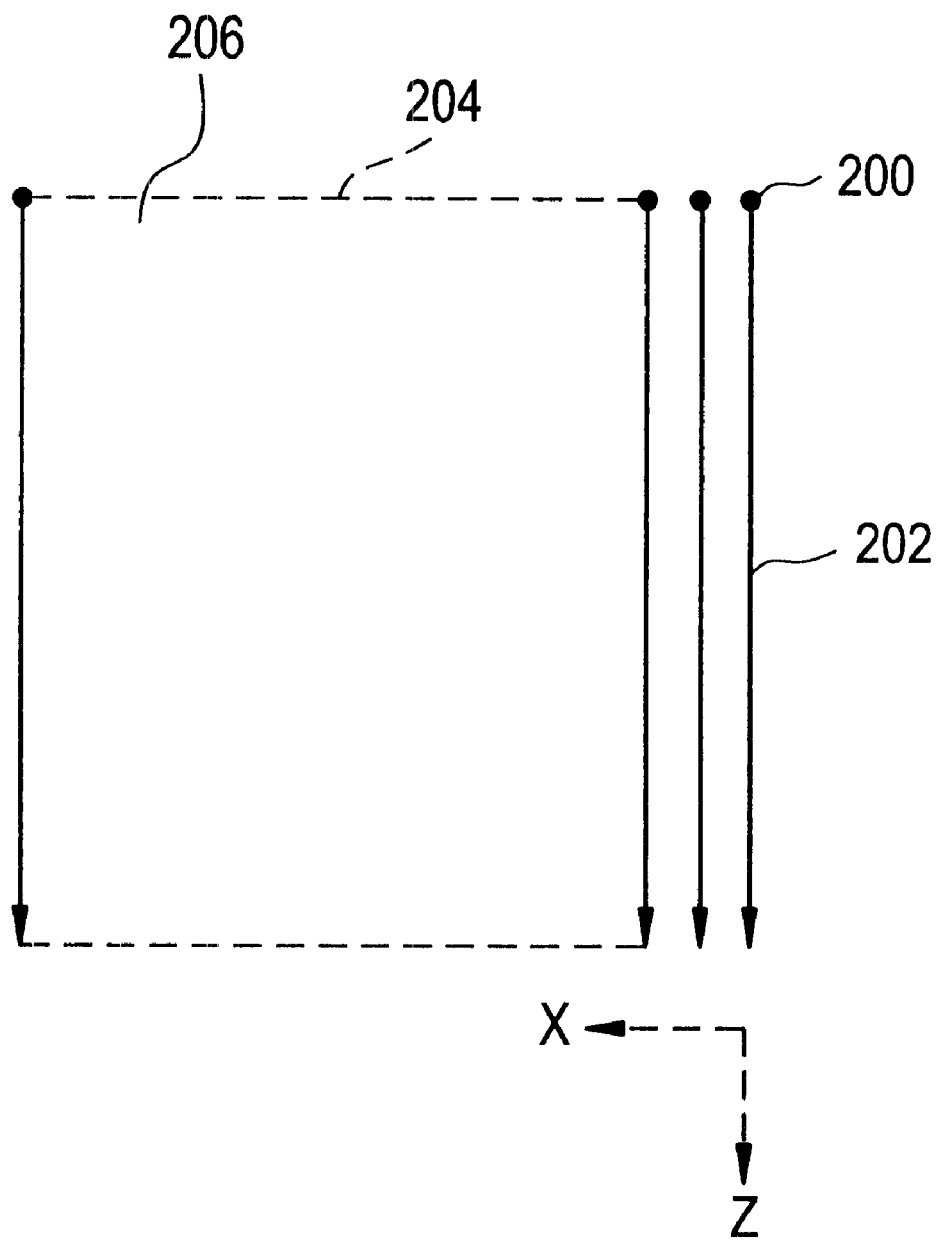
FIG. 4 is a schematic diagram of sonic beam scanning by the apparatus shown in FIG. 1.

When the transmission and reception apertures are formed as part of the ultrasonic transducer array, the apertures are moved in succession along the array, thereby implementing the scanning as shown in FIG. 4 for example. Specifically, the sonic beam 202 which extends in the Z direction from the radiation point 200 is moved along a locus 204 of straight line to scan a two-dimensional rectangular region 206 in the x direction, thereby performing so-called linear scanning.

Figure 5:
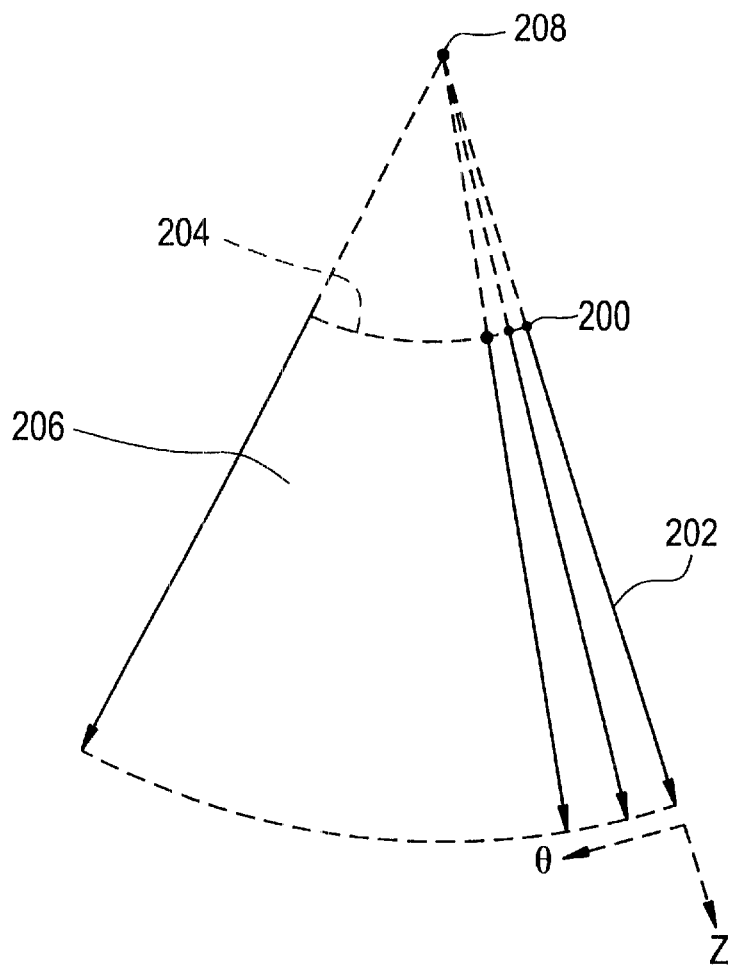
FIG. 5 is a schematic diagram of sonic beam scanning by the apparatus shown in FIG. 1.

When the ultrasonic transducer array is a so-called convex array in which the ultrasonic transducer array is arranged along an arc which is advanced toward the ultrasonic transmission direction, it is obviously possible based on sonic beam scanning similar to linear scanning to scan a two-dimensional sectoral region 206 along the θ direction by moving the radiation point 200 of the sonic beam 202 along an arcuate locus 204 as shown in FIG. 5 for example, thereby performing so-called convex scanning.

The above-mentioned scanning takes place continuously or intermittently under control of the control section 18. The intermittent scanning has an interval of several seconds to several tens of seconds. The portion of apparatus including the ultrasonic probe 2, transmit/receive section 6 and control section 18 is an example of embodiment of the inventive ultrasonic wave transmission/reception means.

The transmit/receive section 6 is connected to a B-mode processing section 10 and Doppler processing section 12. The echo reception signal of each sonic beam released by the transmit/receive section 6 is put into the B-mode processing section 10 and Doppler processing section 12.

Figure 6:
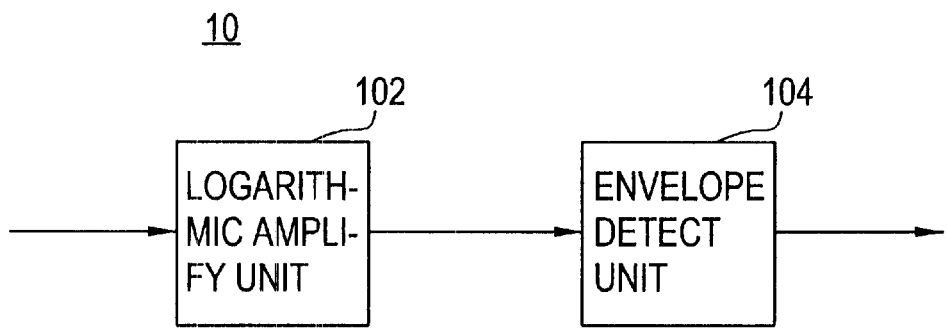
FIG. 6 is a block diagram of the B-mode processing section of the apparatus shown in FIG. 1.

The B-mode processing section 10 functions to produce B-mode image data. The B-mode processing section 10 includes a logarithmic amplify unit 102 and an envelope detect unit 104 as shown in FIG. 6. The B-mode processing section 10 implements with its envelope detect unit 104 the logarithmic amplification for the echo reception signal and implements with its envelope detect unit 104 the envelope detection for the amplified signal thereby to produce a signal indicative of the strength of echo at each reflection point on the sonic beams, i.e., A-scope signal, and produce B-mode image data by sampling the amplitude of the A-scope signal as a value of luminous intensity.

The Doppler processing section 12 functions to produce Doppler image data. The Doppler image data includes flow velocity data, variance data and power data as will be explained later.

Figure 7:
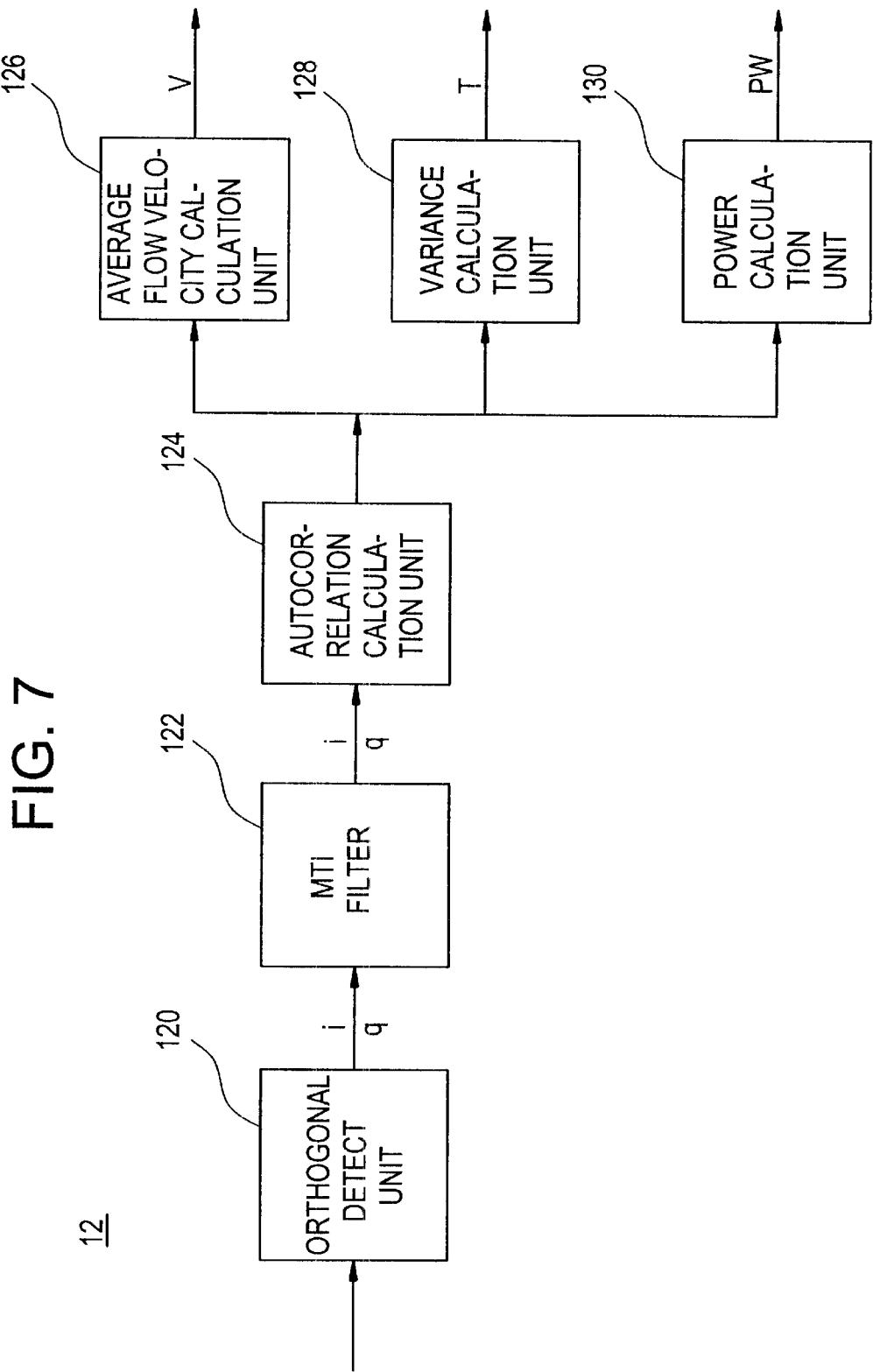
FIG. 7 is a block diagram of the Doppler processing section of the apparatus shown in FIG. 1.

The Doppler processing section 12 has an orthogonal detect unit 120, an MTI (Moving Target Identification) filter 122, an autocorrelation calculation unit 124, an average flow velocity calculation unit 126, a variance calculation unit 128 and a power calculation unit 130, as shown in FIG. 7.

The Doppler processing section 12 implements with its orthogonal detect unit 120 the orthogonal detection for the echo reception signal, and implements with its MTI filter 122 the MTI process to evaluate the Doppler shift of the echo signal. It further implements with its autocorrelation calculation unit 124 the autocorrelation calculation for the output signal of the MTI filter 122, evaluates with its average flow velocity calculation unit 126 the average flow velocity V from the result of autocorrelation calculation, evaluates with its variance calculation unit 128 the variance T of the flow velocity from the result of autocorrelation calculation, and evaluates with its power calculation unit 130 the power PW of the Doppler signal from the result of autocorrelation calculation. Hereinafter, the average flow velocity will be called simply flow velocity, the variance of flow velocity will be called simply variance, and the power of Doppler signal will be called simply power.

The Doppler processing section 12 produces data of each sonic beam indicative of the flow velocity V, variance T and power PW of the echo source in motion in the subject 4. The data indicates the flow velocity, variance and power of each pixel on the sonic beam. The flow velocity represents the component in the sonic beam direction, with the directivity of coming toward or going away from the ultrasonic probe 2 being distinguished.

The B-mode processing section 10 and Doppler processing section 12 are connected to an image processing section 14. The image processing section 14 forms a B-mode image and a Doppler image based on the data provided by the B-mode processing section 10 and Doppler processing section 12, respectively. The arrangement including the B-mode processing section 10, Doppler processing section 12 and image processing section 14 is an example of embodiment of the inventive image forming means.

Figure 8:
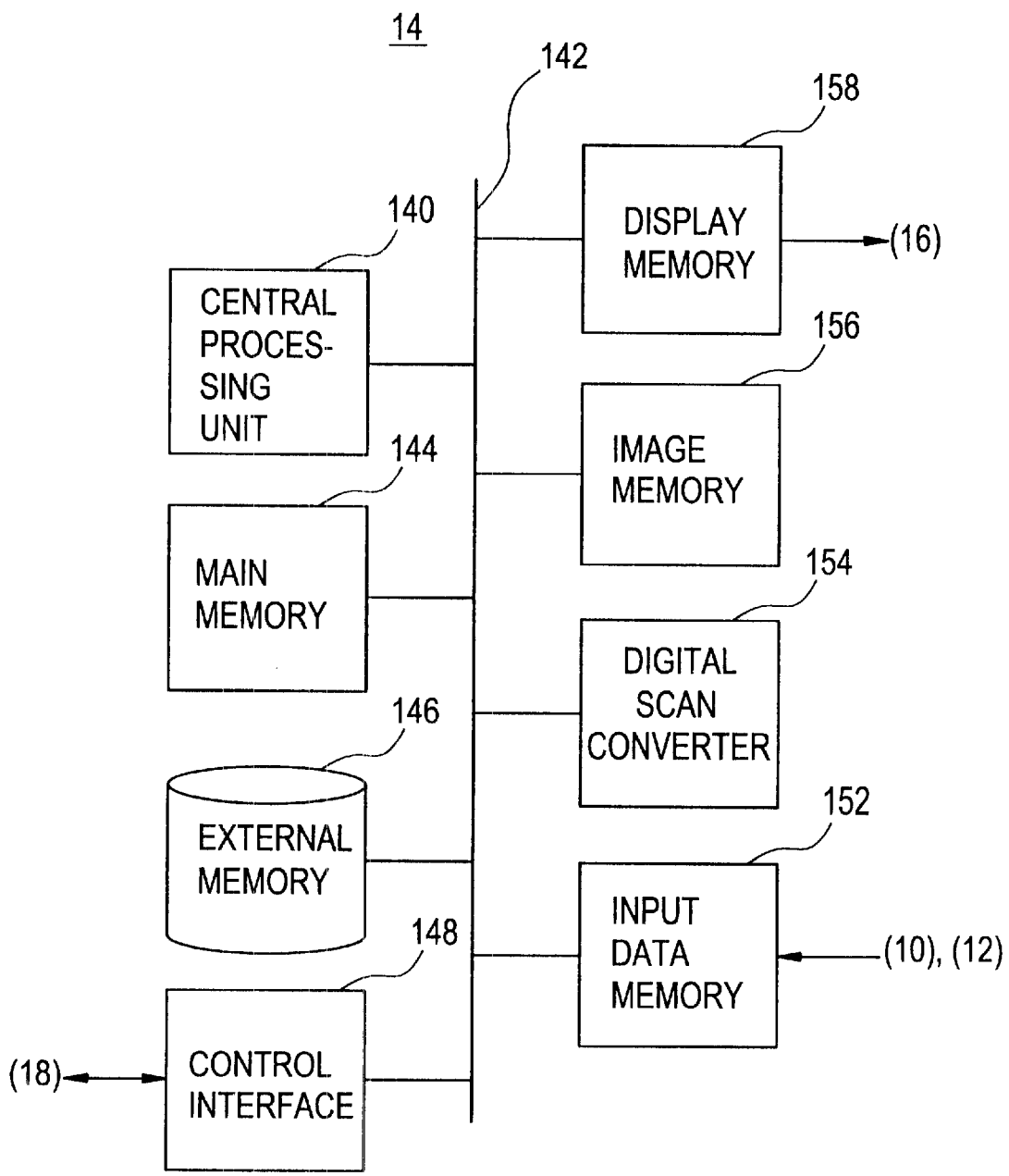
FIG. 8 is a block diagram of the image processing section of the apparatus shown in FIG. 1.

The image processing section 14 has a central processing unit (CPU) 140 as shown in FIG. 8. The CPU 140 is connected by a bus 142 to a main memory 144, an external memory 146, a controller interference 148, an input data memory 152, a digital scan converter (DSC) 154, an image memory 156, and a display memory 158.

The external memory 146 stores a program which is run by the CPU 140. The external memory 146 also stores various data used by the CPU 140 in running the program.

The CPU 140 loads the program from the external memory 146 into the main memory 144, and runs the program to carry out the imaging process. The program stored in the external memory 146 acts on the CPU 140 to accomplish an information display function. During the program execution, the CPU 140 transacts control signals via the controller interference 148 with a control section 18 which will be explained later.

The B-mode image data and Doppler image data provided by the B-mode processing section 10 and Doppler processing section 12 for each sonic beam are stored in the input data memory 152. The data in the input data memory 152 is rendered the scan conversion by the DSC 154 and stored in the image memory 156. The data in the image memory 156 is loaded into the display memory 158 and then fed to a display section 16.

The display memory 158 is further written by the CPU 140 the preceding time indication image which will be explained later. Accordingly, the display section 16 receives the preceding time indication image in addition to the image from the image memory 156.

The image processing section 14 is connected with the display section 16. The display section 16 is supplied with the image signal from the image processing section 14, so that it displays a picture based on the signal. The display section 16 is a graphic display unit having a cathode-ray tube (CRT) which is capable of displaying a color picture. The display section 16 is an example of embodiment of the inventive display means. It is also an example of embodiment of the inventive indication means.

The foregoing transmit/receive section 6, B-mode processing section 10, Doppler processing section 12, image processing section 14 and display section 16 are connected with the control section 18. The control section 18 controls these sectioins by supplying the control signals to them. The control section 18 has inputs of various information signals from the controlled sections. The B-mode operation and Doppler mode operation take place under control of the control section 18.

The control section 18 is connected with an operation section 20. The operation section 20 is operated by the operator to enter timely commands and information to the control section 18. The operation section 20 is an operation panel which is equipped with, for example, a keyboard, pointing device and other operation devices.

The imaging operation of this apparatus will be explained. Continuous scanning without the injection of contrast agent will be explained first. The operator brings the ultrasonic probe 2 to come in contact with an intended portion of the subject 4, and operates the operation section 20 to carry out the imaging operation which covers both the B mode and Doppler mode for example. B-mode imaging and Doppler-mode imaging take place on a time slice basis under control of the control section 18. Specifically, for example, scannings for the B-mode and Doppler mode take place at such a proportion as one B-mode scanning in every certain number of Doppler-mode scanning.

In the B mode, the transmit/receive section 6 operates on the ultrasonic probe 2 to scan the inside of the subject 4 and receive the echo of each sonic beam. The B-mode processing section 10 amplifies with its logarithmic amplify unit 102 the echo reception signal provided by the transmit/receive section 6 and implements the envelope detection with its envelope detect unit 104 to produce the A-scope signal, thereby producing B-mode image data for each sonic beam based on the signal.

The image processing section 14 stores the B-mode image data of each sonic beam provided by the B-mode processing section 10 into the input data memory 152. In consequence, a sonic beam data space for the B-mode image data is formed in the input data memory 152.

In the Doppler mode, the transmit/receive section 6 operates on the ultrasonic probe 2 to scan the inside of the subject 4 and receive the echo of each sonic beam. In this operation, a number of times of ultrasonic wave transmission and reception take place for each sonic beam.

The Doppler processing section 12 implements with its orthogonal detection unit 120 the orthogonal detection for the echo reception signal, implements the MTI process with its MIT filter 122, and evaluates the autocorrelation with its autocorrelation calculation unit 124. It further evaluates the flow velocity V from the autocorrelation result with its flow velocity calculation unit 126, evaluates the variance T with its variance calculation unit 128, and evaluates the power PW with its power calculation unit 130. These calculated values become data indicative of the flow velocity, variance and power of the echo source of each sonic beam and each pixel.

the image processing section 14 stores Doppler image data of each pixel and each sonic beam provided by the Doppler processing section 12 into the input data memory 152. In consequence, a sonic beam data space for each Doppler image data piece is formed in the input data memory 152.

The CPU 140 implements with its DSC 154 the scan conversion for the B-mode image data and Doppler image data in the input data memory 152, and writes the resulting data into the image memory 156.

In this case, the Doppler image data is written as flow velocity distribution image data which is a combination of the flow velocity V and variance T, power Doppler image data with variance which is the power-Doppler image data using the power PW or a combination of the power PW and variance T, and the variance image data using the variance T.

The CPU 140 writes the B-mode image data and each Doppler image data piece into separate areas. The display section 16 displays an image which is based on the B-mode image data and each Doppler image data piece.

The B-mode image becomes a tomographic image of the body tissues on the sonic beam scanning plane. Among the color Doppler images, the flow velocity distribution image becomes an image indicative of a two-dimensional distribution of flow velocity of the echo source. This image has different display colors for different flow directions, has different luminous intensities for different flow velocities, and intensifies certain colors thereby to vary the purity of display colors for different variances.

The power Doppler image becomes an image indicative of a two-dimensional distribution of the power of the Doppler signal. This image reveals the presence of echo sources in motion. The luminous intensity of the display color of the image corresponds to the power. With the variance being combined to it, certain colors are intensified thereby to vary the purity of display colors for different variances.

The variance image becomes an image indicative of a two-dimensional distribution of variance values. This image also reveals the presence of echo sources in motion. The luminous intensity of the display color corresponds to the value of variance.

In the case of displaying these images on the display section 18, the images are merged into the B-mode image in the display memory 158 and the composed image is displayed on the display section 16, and it is possible to observe a color Doppler image which reveals clearly the positional relation with body tissues.

Figure 9:
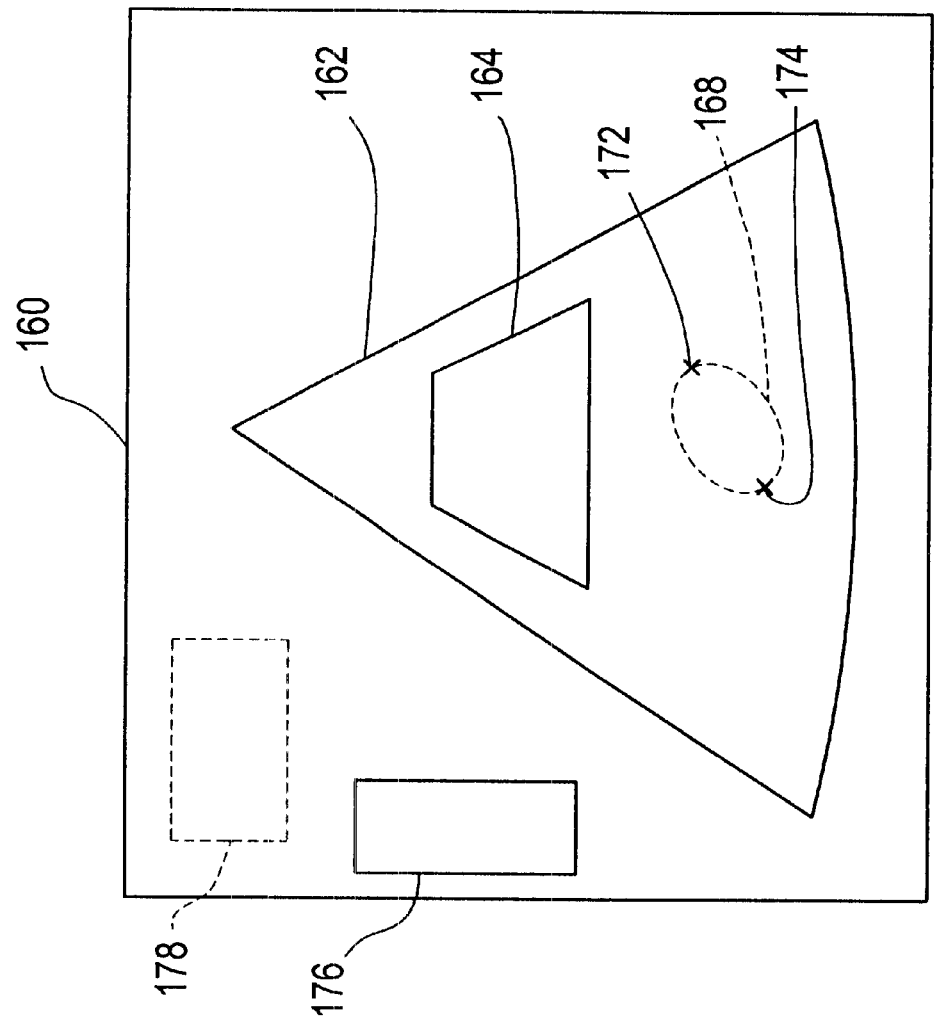
FIG. 9 is a schematic diagram showing an example of display on the display section of the apparatus shown in FIG. 1.

FIG. 9 shows schematically an example of display of the resulting image. As shown in the figure, the screen 160 displays a B-mode image 162 which is taken based on sector scanning. Displayed above the B-mode image 162 is a color Doppler image 164, which is depicted here in terms of the border of a display area.

There is a region of interest (ROI) 168 within the B-mode image 162, with measuring cursors 172 and 174 being displayed at two positions on the profile of ROI. The operator can move the measuring cursors 172 and 174 arbitrarily with the pointing device.

Displayed in the blank area of the screen 160 are a gray scale 176 which indexes the concentration of the B-mode image 162, and a user comment field 176.

Next, imaging based on intermittent scanning will be explained. Intermittent scanning is carried out with the injection of contrast agent 402 to the subject 4.

Figure 10:
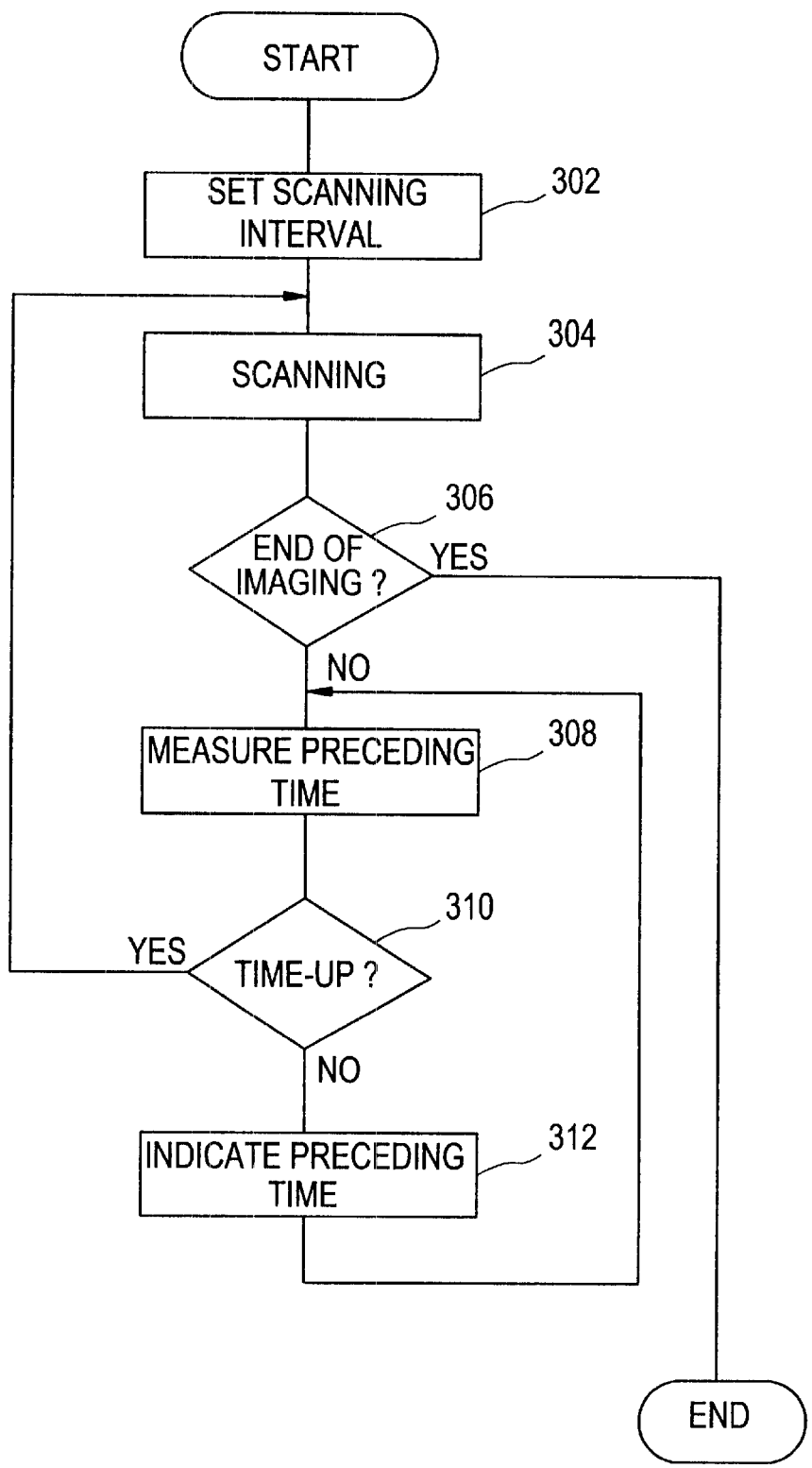
FIG. 10 is a flowchart of the operation of the apparatus shown in FIG. 1.

FIG. 10 shows by flowchart the intermittent scanning operation. As shown in the figure, step 302 sets the interval of scanning. The scanning interval is set by the operator through the operation section 20. The scanning interval ranges from several seconds to several tens of seconds for example.

The next step 304 implements the scanning. Specifically, the sonic beam 206 scans the two-dimensional region 206 only once under control of the control section 18.

The next step 306 judges the end of imaging, and if it is not the end of imaging, step 308 measures the preceding time length under control of the control section 18. The control section 18 measures the preceding time length by counting down the setup value of scanning interval.

The next step 310 judges the expiration, i.e., count 0, of the preceding time length, and unless it is time-up, step 312 indicates the preceding time length.

The preceding time length is indicated on the display section 16 under control of the control section 18. The manner of preceding time indication will be explained later. The operations of steps 308 to 312 are repeated, while the preceding time length is measured and indicated, until it expires.

In response to the time-up, the operation sequence returns to step 304 to scan the two-dimensional region 206 once and subsequently measure and indicate the preceding time length as described above. These operations are repeated. On completion of imaging, when the operator takes the imaging terminating operation, the operation ends in response to the judgement of step 306.

Figure 11:
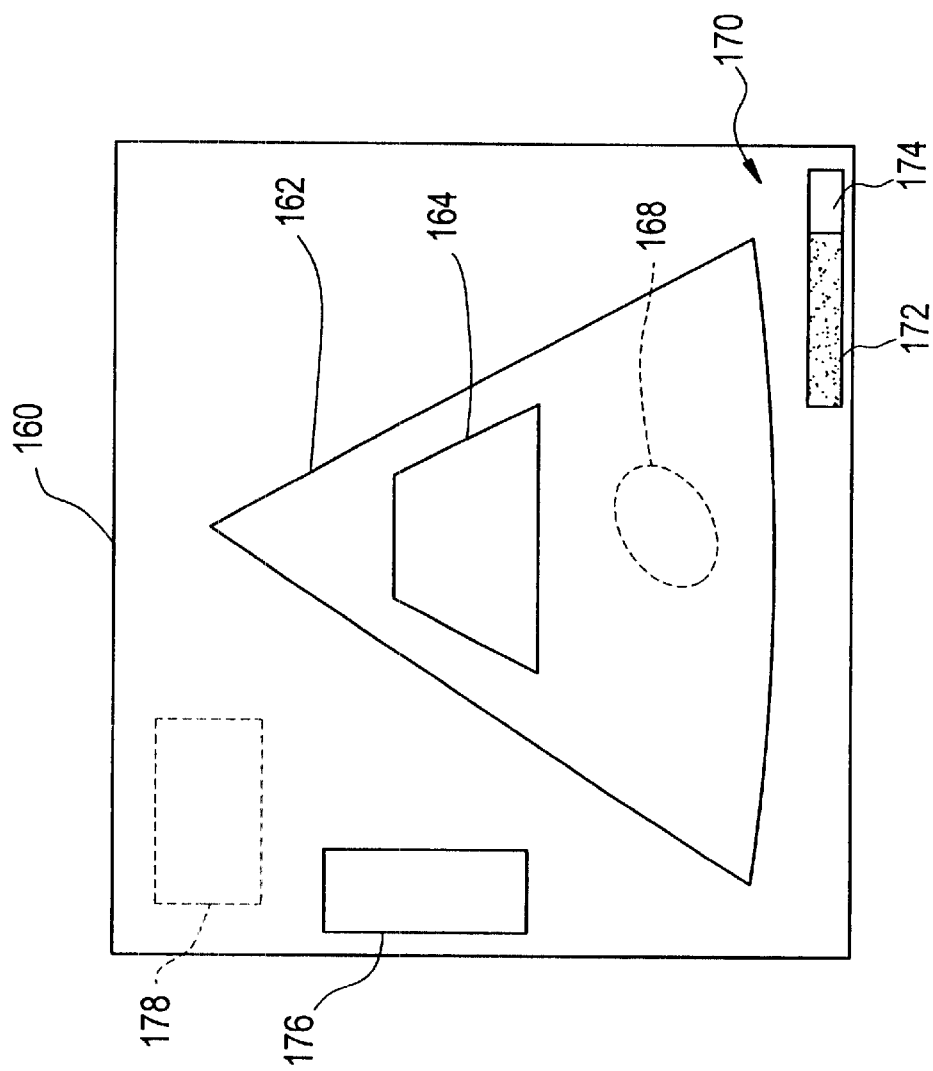
FIG. 11 is a schematic diagram showing an example of display on the display section of the apparatus shown in FIG. 1.

FIG. 11 shows schematically an example of display of intermittent scanning. As shown in the figure, the screen 160 displays a B-mode image 162 which is taken based on sector scanning. Displayed above the B-mode image 162 is a color Doppler image 164.

Within the B-mode image 162, there is a region of interest (ROI) 168, which is filled with contrast agent. Displayed in the left-hand blank area of the screen 160 are a gray scale 176 which indexes the concentration of the B-mode image 162, and a user comment field 187.

As a result of intermittent scanning, the B-mode image 162 and color Doppler image 164 are revised intermittently. During the scan resting period between intermittent scannings, these images are displayed as still or frozen images. The scan resting period is equal in length to the scanning interval.

Displayed in the bottom-right blank area of the screen is a bar graph 170, which is an example of the preceding time indication image. The bar graph 170 is a figure of horizontal strip having a constant length irrespective of the value of scanning interval. The bar graph 170 may have its length varied in proportion to the scanning interval.

The bar graph 170 consists of two sections 172 and 174 of different levels of brightness. The dark section 172 increases in length and the bright section 174 decreases in length with the passage of scan resting period.

The operator can known the passage of scan resting period in terms of the proportion of the length of the dark section 172 out of the resting period. The operator can known the preceding time which lasts until the start of the next scanning in terms of the proportion of the length of the bright section 174 out of the resting period. If the bar graph 170 has a length which is proportional to the scanning interval, the operator can known the time passage and the preceding time length in terms of absolute values.

The bar graph 170 may consist of two sections of different hues instead of levels of brightness. The bar graph 170 may be displayed vertically in the right-hand blank area of the screen for example.

In consequence, the operator can recognize the next scanning start time accurately in analog fashion, and can relax and wait in most of the resting period. Accordingly, the operator can be relieved of the mental and physical duty.

Figure 12:
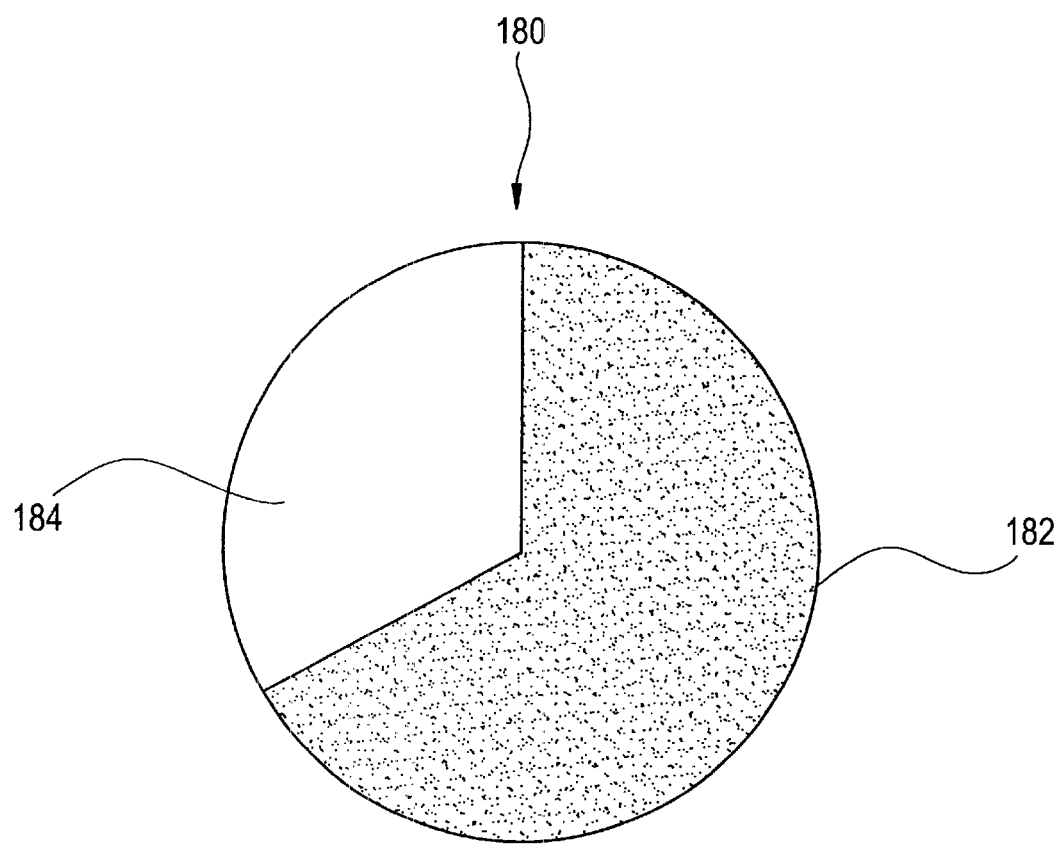
FIG. 12 is a schematic diagram showing an example of the preceding time display image.

The preceding time indication image may be a sector graph 180 as shown in FIG. 12. The sector graph 180 is designed to consist of two sectors 182 and 184 of different levels of brightness, with the dark sector 172 increasing in area and the bright sector 174 decreasing in area with the passage of scan resting period. The operator can recognize the preceding time length in terms of the area of the bright sector 174 in analog fashion. The levels of brightness may be substituted by hues as in the case of FIG. 11.

Figure 13:
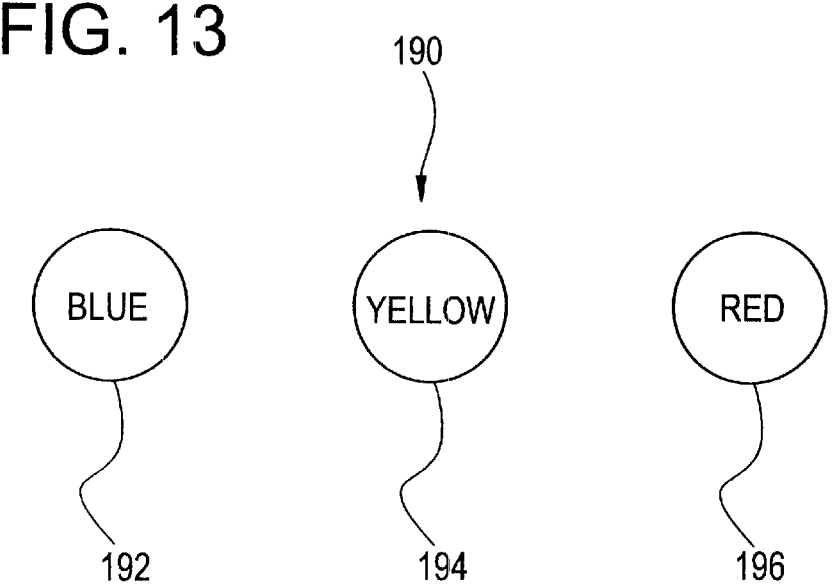
FIG. 13 is a schematic diagram showing an example of the preceding time display image.

The preceding time indication image may be a set of three color signal display images 190 similar to the traffic signals as shown in FIG. 13. The color signal display images 190 include a blue signal image 192, yellow signal image 194 and red signal image 196.

While the time passage is less than ⅓ of the resting period, the blue signal image 192 is displayed in blue and other images are displayed in white. While the time passage is more than ⅓ and less than ⅔ of the resting period, the yellow signal image 194 is displayed in yellow and other images are displayed in white. When the time passage is more than ⅔ of the resting period, the red signal image 196 is displayed in red and other images are displayed in white. In this manner, the operator can know the preceding time length by display color in steps.

The preceding time length can obviously be displayed numerically instead of graphic display described above, enabling the operator to recognize the preceding time length in digital fashion.

Figure 14:
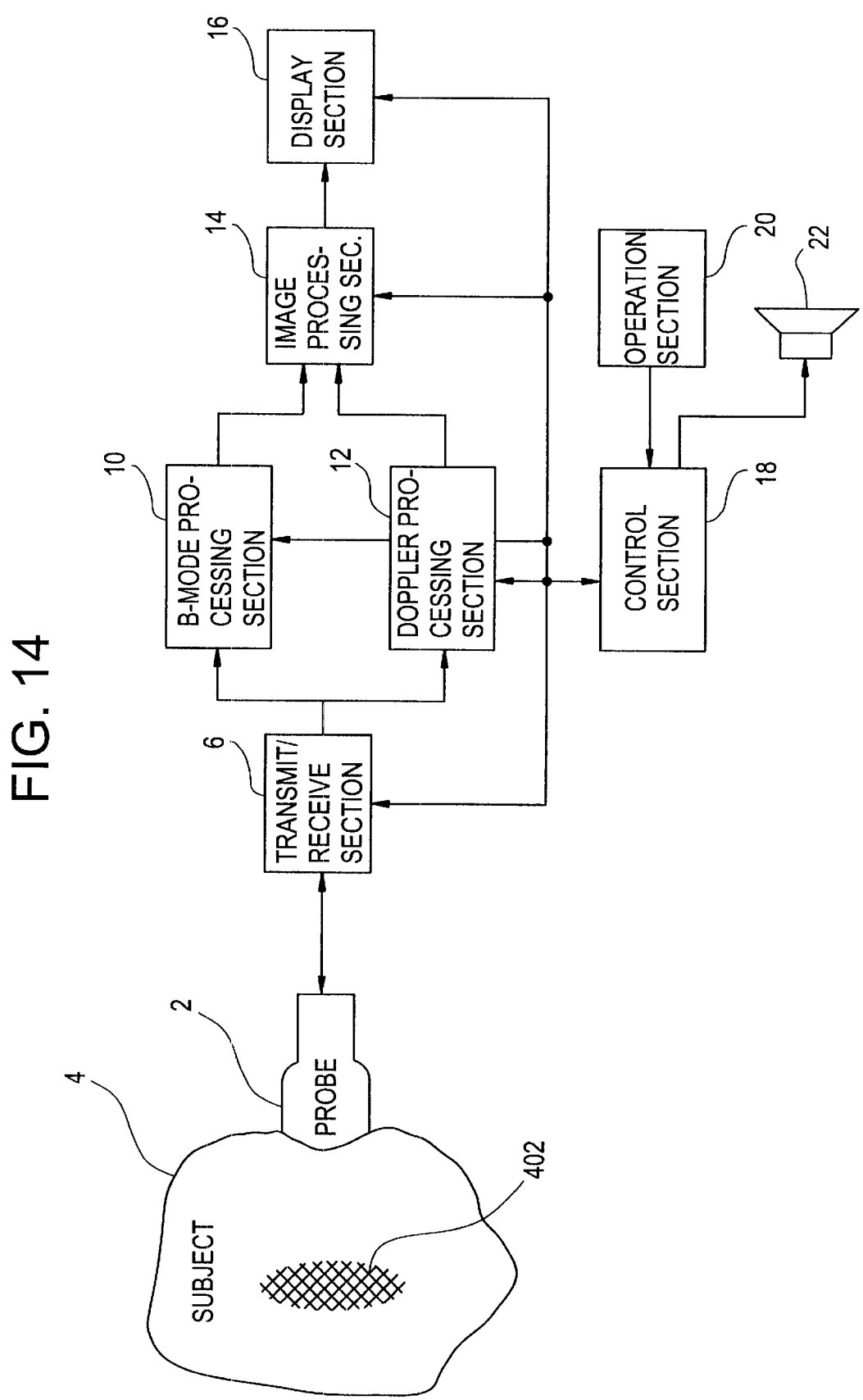
FIG. 14 is a block diagram of the apparatus which is an example of embodiment of this invention.

Otherwise, the preceding time length may be indicated acoustically by the provision of an acoustic output section 22 which is controlled by the control section 18 as shown in FIG. 14. The acoustic output section 22 is an example of embodiment of the inventive indication means.

The acoustic indication takes place at every ten seconds until five seconds to the commencement of scanning, and at every second after five seconds to the commencement of scanning. The indication at every second may be based on either a call of a number of second or a rhythmic sound of one-second period.

The acoustic indication enables the person under test as the subject 4 to anticipate the next scanning start time, and the person can relax and wait during the resting period. Accordingly, the person can also be relieved.

Many widely different embodiments of the invention may be configured without departing from the spirit and the scope of the present invention. It should be understood that the present invention is not limited to the specific embodiments described in the specification, except as defined in the appended claims.

What is claimed is:

1. A method of indicating a time period between scans in an ultrasonic imaging procedure, said method comprising the steps of:

setting a particular time period between a first imaging scan of ultrasonic waves and a second imaging scan of ultrasonic waves;

performing a first imaging scan of ultrasonic waves followed by said particular time period and then followed by said second imaging scan of ultrasonic waves;

producing an image based on received echoes corresponding to said first and second imaging scans of ultrasonic waves; and indicating in real time said particular time period between said first imaging scan of ultrasonic waves and said second imaging scan of ultrasonic waves, and time remaining in said particular time period after performing of said first imaging scan of ultrasonic waves and until said second imaging scan of ultrasonic waves.

2. The method of claim 1, wherein said indicating is provided by a line graph.

3. The method of claim 1, wherein said indicating is provided by a bar graph.

4. The method of claim 1, wherein said indicating is provided by a sector graph.

5. The method of claim 1, wherein said indicating is provided by different hues of color.

6. The method of claim 1, wherein said indicating is provided by digital numbers.

7. The method of claim 1, wherein said indicating is provided acoustically.

8. An ultrasonic imaging apparatus comprising:

means for setting a particular time period between a first imaging scan of ultrasonic waves and a second imaging scan of ultrasonic waves;

means for performing a first imaging scan of ultrasonic waves followed by said particular time period and then followed by a second imaging scan of ultrasonic waves;

means for producing an image based on received echoes corresponding to the performing of said first and second imaging scans of ultrasonic waves; and means for indicating in real time said particular time period between said first imaging scan of ultrasonic wave and, said second imaging scan of ultrasonic waves, and time remaining in each said particular time period after performing of said first imaging scan of ultrasonic waves and until said second imaging scan of ultrasonic waves.

9. The apparatus of claim 8, wherein said means for indicating comprises means for displaying a line graph.

10. The apparatus of claim 8, wherein said means for indicating comprises means for displaying a bar graph.

11. The apparatus of claim 8, wherein said means for indicating comprises means for displaying a sector graph.

12. The apparatus of claim 8, wherein said means for indicating comprises means for displaying different hues of color.

13. The apparatus of claim 8, wherein said means for indicating comprises means for displaying digital numbers.

14. The apparatus of claim 8, wherein said means for indicating comprises acoustic means.

* * * * *